March 30, 1976 A. GROB Plant Pat. 3,854
KALANCHOE PLANT
Filed Sept. 25, 1974
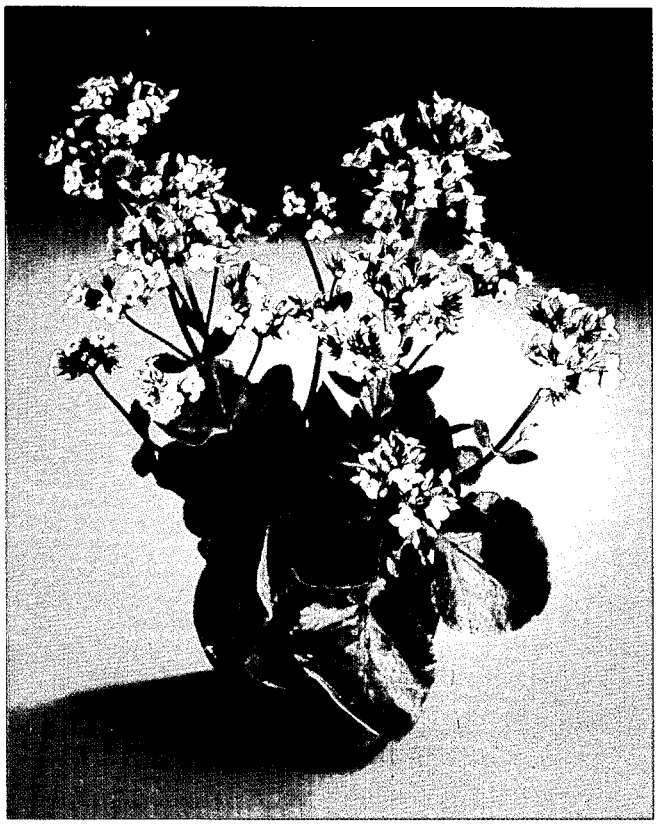

United States Patent

Plant Pat. 3,854
Patented Mar. 30, 1976

1

3,854
KALANCHOE PLANT

Adolf Grob, St. Gallen, Switzerland, assignor to
Mikkelsens Inc., Ashtabula, Ohio Filed Sept. 25, 1974, Ser. No. 509,146
Int. Cl. A01h 5/00
U.S. Cl. Plt.—68 1 Claim The present invention relates to a new and distinct variety of Kalanchoe plant known by the varietal name Gelbe Melody.

The new variety was discovered by me as a mutation of the cultivar Grobs Melody Red, from a seedling of the parent cultivar. The mutation was noted by virtue of its striking yellow flower color, as contrasted with the red flower color of the parent cultivar.

The new cultivar was first asexually reproduced by vegetative cuttings at St. Gallen, Switzerland, and the unique characteristics of the new cultivar have been transmitted through successive propagations.

The new cultivar is particularly characterized by its tight and medium high growth habit, rounded foliage, relatively long flowering season and strong growing traits. To date, to the best of my knowledge, the new cultivar is the best yellow Kalanchoe variety available for commercial production.

With respect to the earlier cultivar Sternschnuppe, an unpatented cultivar and perhaps the closest cultivar for comparison purposes, the new cultivar has a more tight plant structure and a longer flowering period.

The following description is based on plants of the new cultivar grown initially in St. Gallen, Switzerland, and subsequently in Ashtabula, Ohio. Flower color and foliage values are taken from the RHS Colour Chart.

The accompanying color photographic drawing shows a typical blooming plant of the new cultivar, with the color being as true as possible with color illustrations of this type.

Parentage: The new cultivar is a mutation of Grobs Melody Red, an unpatented cultivar.

Propagation: By asexually propagating by cuttings, it has been successfully demonstrated that the new cultivar is stable and produces true to type.

Form: Bush form; medium branched; upright and medium to tall; strong stems.

Growth habit: Medium vigor; upright and branching.

Rooting: The roots of the new cultivar are strong.

Blooming habit: Reacts well to short day treatment under controlled cultural practices; quick flower initiation under controlled cultural practices; quick flower initiation under controlled daylength; response period 12 weeks in summer and 14 weeks in winter.

Blooming season: Natural blooming season is January–February, although by short day treatment, flowering of the cultivar is possible year around.

2

Foliage: Leaves are opposite; quanttiy of leaves would be considered below average because of long internodes. Some tendency of tissue outgrowths to develop a long vein near base of leaf during winter months if nitrogen level is too high.

*Size.*—Average size leaves on plants grown during fall to summer months, approximately 5 cm. wide and 8 cm. long. Compared to the unpatented Kalanchoe cultivar Mace, the size of the leaves would be considered small.

*Shape.*—From obovate to oval.

*Texture.*—Smooth, thick, crisp, coriaceous.

*Margin.*—Some tendency to revolute.

*Color.*—Upperside between green 139A and yellow green 147A. Lowerside approximately yellow green 147B.

Disease resistance: When grown with the Kalanchoe cultivars Exotic Yellow and Exotic Gold which are quite susceptible to mildew, Gelbe Melody is not affected.

Flowers:

*Borne.*—On a nearly flat topped compound cyme. Main flower stalks are heavy and strong, being 15 cm. to 20 cm. long from point of origin. Length of flower stalks can be manipulated by growth regulators or by timing the removal of the apex relative to the start of short day treatment for any particular seasonal environment.

*Quantity.*—Is normal for Kalanchoes. Flowering of first buds to last buds extends upwards of 60 days.

*Flower buds.*—Are light yellow-green, approximately 148C covered by four sepals before opening. Buds measure 4 to 6 mm. just before petals begin to emerge.

*Petals.*—Four petals are nearly round with a short central point at outer edge, and measure 6 mm. in diameter. Total individual flower diameter 15 mm.; color yellow 7A, fading to 12C.

Reproductive organs:

*Stamens.*—Eight in number, in two sets of four, yellow anthers, light green filaments.

*Pollen.*—Light yellow, released in two stages.

*Styles/ovaries.*—Four styles, stigmas light green turning white when receptive, four ovaries each developing multiple brown seed.

I claim:

1. A new and distinct cultivar of Kalanchoe characterized particularly by its yellow flower color, tight structure, relatively long flowering period, rounded foliage, and strong growth habit.

No references cited

ROBERT E. BAGWILL, Primary Examiner

UNITED STATES PATENT AND TRADEMARK OFFICE

CERTIFICATE OF CORRECTION

PATENT NO. : PP-3854

DATED : March 30, 1976

INVENTOR(S) : ADOLF GROB

It is certified that error appears in the above-identified patent and that said Letters Patent are hereby corrected as shown below:

Column 1, lines 49-50, delete "quick flower initiation under controlled cultural practices;".

Signed and Sealed this

*twenty-ninth* Day of *June 1976*

[SEAL]

*Attest:*

RUTH C. MASON
*Attesting Officer*

C. MARSHALL DANN
*Commissioner of Patents and Trademarks*